United States Patent
Klaas

(10) Patent No.: US 6,960,770 B2
(45) Date of Patent: Nov. 1, 2005

(54) METHOD AND DEVICE FOR DETERMINING ANY FLUID MIXTURE COMPOSITION AND FOR MEASURING MATERIAL QUANTITY

(76) Inventor: Kai Klaas, Tannenstrasse 18, 79761 Waldshut-Tiengen (DE)

( * ) Notice: Subject to any disclaimer, the term of this patent is extended or adjusted under 35 U.S.C. 154(b) by 113 days.

(21) Appl. No.: 10/276,580

(22) PCT Filed: May 14, 2001

(86) PCT No.: PCT/EP01/05450

§ 371 (c)(1), (2), (4) Date: Jun. 30, 2003

(87) PCT Pub. No.: WO01/88508

PCT Pub. Date: Nov. 22, 2001

(65) Prior Publication Data

US 2004/0046122 A1 Mar. 11, 2004

(30) Foreign Application Priority Data

May 13, 2000 (DE) .......................... 100 23 639

(51) Int. Cl.[7] ............................................. G01N 21/35
(52) U.S. Cl. ..................................................... 250/343
(58) Field of Search ...................................... 250/341.1

(56) References Cited

U.S. PATENT DOCUMENTS

| | | | | |
|---|---|---|---|---|
| 4,687,337 A | * | 8/1987 | Stewart et al. | 356/437 |
| 5,057,691 A | * | 10/1991 | Kaihara et al. | 250/339.11 |
| 5,350,922 A | * | 9/1994 | Bartz | 250/338.5 |
| 5,898,487 A | * | 4/1999 | Hage | 356/36 |
| 5,994,150 A | * | 11/1999 | Challener et al. | 436/518 |

FOREIGN PATENT DOCUMENTS

DE         EP0539824 A2   *   5/1993   .......... G01N/21/25

* cited by examiner

Primary Examiner—David Porta
Assistant Examiner—Marcus Taningco
(74) Attorney, Agent, or Firm—Bachman & LaPointe, P.C.

(57) ABSTRACT

A method for determining any fluid mixture composition and for measuring material quantity by detecting light absorption, especially infrared light, emitted by an emitter (12.1, 12.2) in a fluid to be analyzed having non absorbed and non reflected components that are detected by a receptor (18.1, 18.2). According to said method, light is emitted directly from the emitter (12.1, 12.2) to the receptor (18.1, 18.2) through said fluid. Additionally, the light going through a channel (10, 16) before and/or after the fluid is dispersed at least once. The distance between emitter (12.1, 12.2) and receptor (18.1, 18.2) can be continuously altered. Electronic components are provided with a switch enabling to remove any interference light.

23 Claims, 3 Drawing Sheets

METHOD AND DEVICE FOR DETERMINING ANY FLUID MIXTURE COMPOSITION AND FOR MEASURING MATERIAL QUANTITY

The invention relates to a method for determining the mixture composition of a liquid by means of determining the absorption of light, in particular infrared light, which is emitted by a transmitter in a housing into the medium to be examined and whose nonabsorbed or nonreflected components are registered by a receiver in a housing, the light being sent through the medium directly from transmitter to receiver.

In many sectors, in particular industrial sectors, it is necessary to determine the mixture composition of a medium or the quantity of a material. Purely by way of example, reference should be made to turbidity measurement in water treatment, determining the mixture composition in the foodstuffs industry, chemical and pharmaceutical industry, paper industry, textile industry, for example the level of dyeing of a textile, the beverage industry, mining, etc., and to measuring the quantity of a material, for example when determining thin sheet thicknesses.

At present, use is substantially made of two methods, the scattered light measuring method and the transmitted light measuring method. In turbidity measurement (turbidimetry), for relatively low turbidities the measurement of the scattered radiation power (scattered light method) is better suited. In the case of this nephelometry, light is radiated into the medium to be examined and is scattered at particles contained therein. The intensity of the scattered light, which leaves the measuring cell at a specific angle (normally 90°), is measured by a photodiode.

In the case of relatively high turbidities, on the other hand, the transmitted light measuring method is better suited which measures photometrically the decrease in radiation power during passage through the medium.

The disadvantage with all the known measuring instruments on the market is that it is not possible to measure both particularly weakly absorbing and particularly strongly adsorbing media. Because of the principle, for example, highly absorbent media cannot be measured by the scattered light method, since the light even cannot penetrate into the medium. On the other hand, if the distance between transmitter and receiver is too great in the transmitted light measuring method, then in the case of very highly absorbent media, this likewise leads to failure of the measuring principle (in the case of too high a distance, there is simply no measured signal which can be used).

Furthermore, in many instruments, the transmitter normally comprises only a single transmitting diode. Because of the cross-sectional area of the measuring beam which is present in this case and much to small, even extremely small inhomogeneities or granularities of the medium lead to wide fluctuations in the measured signal. In addition, such a measuring instrument is extremely sensitive to deposits on the transmitting or receiving diode.

Furthermore, the tiny extent of the measuring beam and the highly inhomogeneous radiation field make it virtually impossible to align the transmitter and receiver in the case of a variable arrangement. Extremely small deviations from this alignment, for example caused by vibrations or impacts, would result in drastic measured signal changes and erroneous calibrations.

EP-A 0 029 537 discloses a method for the detection of particles in a gas stream. In this case, the particles fly through a laser beam. The change in the intensity of light is registered by a photoelectric sensor.

EP-A 0 463 166 discloses a device for measuring the optical density of gas. In this case, a radiator, a measuring flow chamber and a photoreceiver are accommodated along an optical axis. By means of this device, the analysis of the optical density of motor vehicle exhaust gases is preferably carried out.

U.S. Pat. No. 4,687,337 concerns the determination of the coefficient of an atmospheric aerosol. This is likewise done by determining the change in a light beam.

U.S. Pat. No. 5,572,032 describes an instrument for analyzing gas, with which two or more components can be determined simultaneously. The corresponding device comprises two measuring cells, light sources, gas filter cells and so on.

A method of the abovementioned type is disclosed by EP-A 0 539 824. This shows a spectrometer for forming turbidimetric and calorimetric measurements. Provided in an appropriate housing is a light source which sends light through appropriate optics and a filter. The light then passes through the sample to be determined. The light passing through the sample is collected by a detector. By contrast, a second detector observes a reference light beam, so that a comparison can be made between reference light beam and the light which has gone through the sample.

The present invention is based on the object of developing a method and a device of the aforementioned type with which both particularly weakly absorbing and particularly highly absorbing media can be measured and, in particular, stray light can almost completely be disregarded.

The features as claimed in claim 1 lead to the achievement of this object.

In a corresponding device, transmitter and/or receiver are inserted into the interior of a housing, remote from a housing opening. This avoids direct stray light striking the receiver, in particular, and therefore distorting the measured result. For this reason, transmitter and/or receiver are also arranged in a preferably rod-like housing, these preferably rod-like housings being approximately parallel to each other, so that the housing openings of transmitter and receiver are located laterally opposite each other. The medium can move freely between the rods, but entry of direct stray light is ruled out to the greatest possible extent.

In order to suppress stray light still further, it may prove to be expedient to color the interior of the respective channels belonging to transmitter and receiver black. In this way, reflection of stray light onto the receivers is avoided.

The distance between transmitter and receiver can be varied. In the present invention, this is done by the appropriate housings themselves being displaced. The change in the distance can preferably be made continuously.

The ability to vary the distance is an essential point in the present invention. It makes it possible for a very close spacing to be selected in the case of highly absorbent material, while the two housings are located further away from each other in the case of less absorbent material.

The absorption coefficients of the respective media can fluctuate over such a large range that measuring instruments with a fixed spacing cannot be brought to cover a similarly large range of absorption coefficients, even with the most complicated electronics, as the present invention. The ability to vary the spacing continuously makes it possible for the first time ever to adapt the measurement range of the measuring instrument on site to the range of fluctuation of the absorption coefficient of the respective medium. Otherwise, precisely in the case of very highly absorbent media, several identical measuring instruments, which differ merely in the spacing between transmitter and receiver, in a grid of 0.5 mm, for example, would have to be tried out until the optimum spacing was found.

In the case of the housings, a metal, in particular stainless steel, is preferably chosen for the housing material. This has the advantage that it adapts very quickly to the temperature of the medium to be measured and, as a result, measured results cannot be distorted by temperature differences between the two preferably rod-like housings, more precisely the electronics situated therein. Furthermore, these steel tubes, together with the other metal housing parts, form a coherent, virtually completely closed Faraday cage, so that even extremely weak signals can be processed without interference and crosstalk.

In a particularly preferred exemplary embodiment of the invention, a small part of the light is branched off after the transmitter and fed to a dedicated circuit. This quantity of light is used as a comparative quantity with the quantity of light determined by the receivers after the passage of the light through the medium to be measured.

It has proven to be expedient to homogenize the light which passes through the medium and which, in the present invention, has a preferably large cross-sectional area. For this purpose, weakly or highly scattering filter disks are provided at suitable points, which eliminate the known hotspots (inhomogeneities in the radiation field) of infrared light transmitters. Accordingly, the receivers are also arranged at a certain distance behind the scattering filter disks, in order to receive this homogenized light to a suitable extent. The receivers for the main quantity of light and also for the quantity branched off are preferably receiver diodes, these receiver diodes being arranged symmetrically behind the respective filter disk. In this case, four receiver diodes arranged distributed have proven to be best.

Without eliminating the hotspots and without the large-area measuring field preferably used in this invention, there would be high fluctuations in the measured signal in the case of granular or otherwise inhomogeneous media.

In order to increase sensitivity of the entire device, it has proven to be expedient to reduce the electric field lines between transmitter and receiver to a minimum. According to the invention, this is done by arranging a metal grating between transmitter and receiver, the metal grating letting through 80% to 90% of the light but only 1% to 0.1% of the electric field lines. This sensitivity is further improved by the light passing through the metal grating being deflected in the channel in front of the receivers. This is done by means of an appropriately arranged deflection mirror.

In each case a circuit for suppressing stray light should be arranged downstream of the receivers. In a preferred exemplary embodiment, a current-voltage converter is in each case followed by a prefilter with frequency-selective amplification and constant-light suppression, a lock-in amplifier, a low-pass filter, an amplifier with interference signal limitation, the respective amplifiers with interference signal limitation then being connected to a common logarithmic amplifier. This logarithmic amplifier is followed by the output circuit, which has two outputs, one for the more highly absorbent material component of a mixture composition, the other for the more weakly absorbing material component.

The two outputs (0 . . . 10V) can be balanced quite simply for most media. Balancing is carried out with two substance samples which have a different and known mixture composition. By rotating two setting potentiometers, the desired output voltage is set.

By using this device according to the invention, far "more opaque" substances can be measured than hitherto.

Of course, the device according to the invention also meets the requirements of DIN EN 27027 and 150 7027.

Further advantages, features and details of the invention emerge from the following description of preferred exemplary embodiments and by using the drawing; in the latter:

A device according to the invention for determining the solids and/or liquid content, in particular the water content, of a liquid medium or, in more general terms, for determining the mixture composition of any desired media or for measuring the quantity of a material has a basic housing 1 in which there is a circuit described further below. Seated on the basic housing 1 are two preferably rod-like housings 2 and 3, which are arranged at a distance d from each other. The medium to be examined can flow or move in an interspace 4 between the two housings 2 and 3. The distance d is otherwise to be adjustable continuously preferably between 0 and 50 mm.

Figure 1:
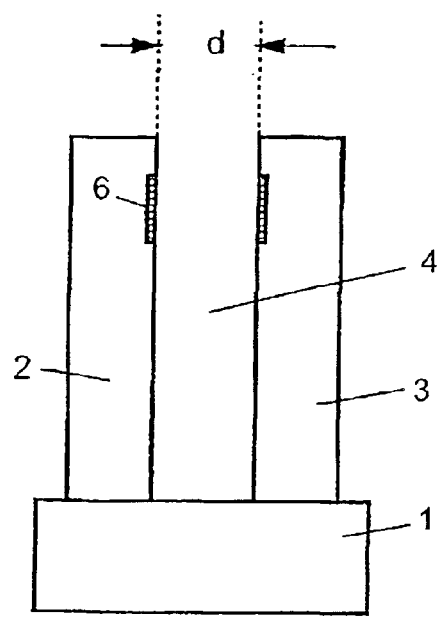
FIG. 1 shows a plan view of a device according to the invention for determining the solids and/or liquid content, in particular the water content, of a liquid medium.
Figure 2:
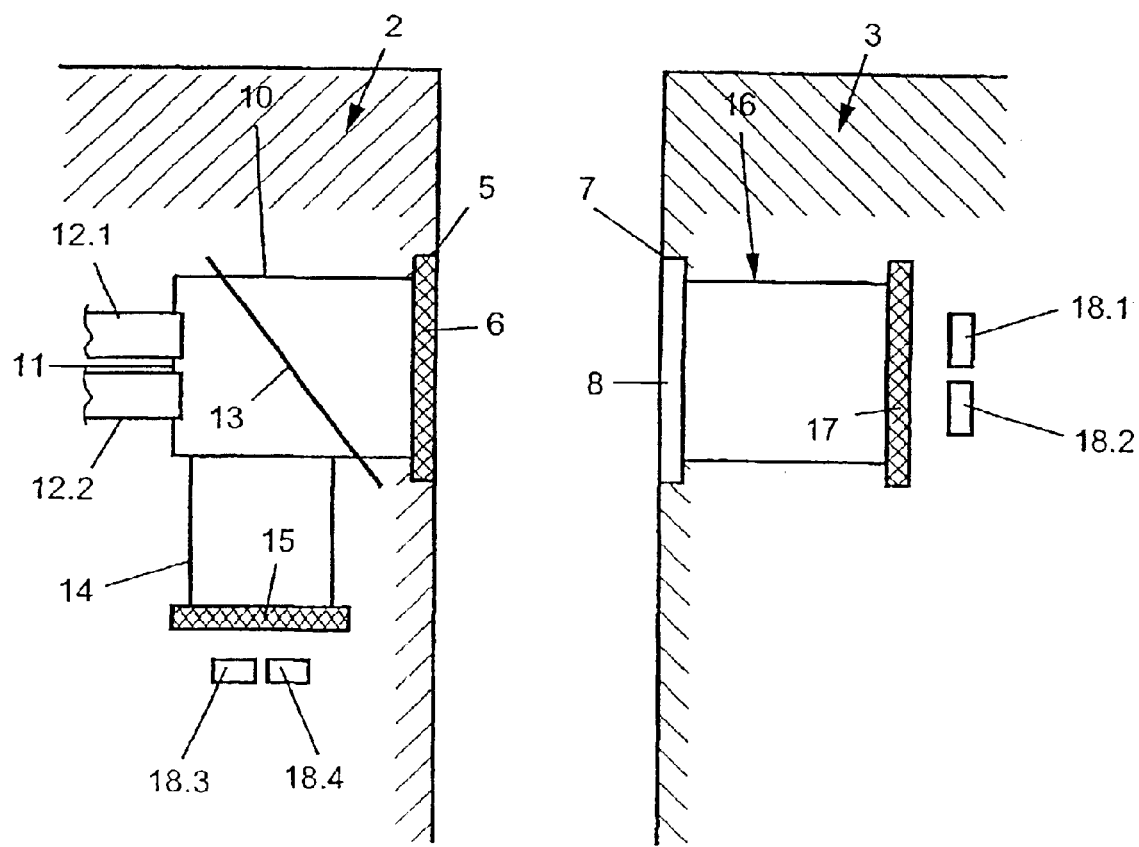
FIG. 2 shows a partial and schematically illustrated detail of the device according to FIG. 1.

According to FIG. 2, the housing 2 has a housing opening 5, into which a filter disk, preferably a weakly scattering disk 6, is inserted. Opposite this filter disk 6, in a further housing opening 7 of the housing 3, there is a transparent disk 8, in particular a glass disk (or else a quartz or sapphire disk).

In the interior of the housing 2, the filter disk 6 is adjoined by a channel 10, into the base 11 of which transmitters 12.1 and 12.2 are let, preferably emitting an infrared light. This infrared light, which is preferably generated by four symmetrically arranged transmitters, strikes a transparent mirror disk 13 before it passes through the filter disk 6, a small part (about 10%) of the infrared light being deflected into a further channel 14, passing through a preferably highly scattering filter disk 15 and being picked up by receivers 18.3 and 18.4. These receivers 18.3 and 18.4 are preferably receiver diodes, four such receiver diodes preferably being arranged symmetrically behind the filter disk 15.

Both the filter disk 6 and the filter disk 15 have the task of evening out hotspots (asymmetries in the radiation field), which occur in infrared transmitters, and in this way of homogenizing the entire beam.

Opposite the filter disk 6, the glass disk 8 is likewise followed by a channel 16, which is in turn closed off by a highly scattering filter disk 17. Behind this filter disk 17 there are preferably four receivers (receiver diodes), only two receivers 18.1 and 18.2 being shown. This filter disk 17 also has the purpose of evening out the radiation and of transmitting it in a form evened out in this way to the four photo receivers.

Incidentally, the housings 2 and 3 preferably consist of steel tubes, which achieves evening out of the heat, regardless of the medium with which the housings come into contact. The housings 2 and 3 reach the temperature of the medium after an extremely short time. All the receiver diodes 18.1, 18.2, 18.3 and 18.4 are therefore virtually always at the same temperature.

Figure 3:
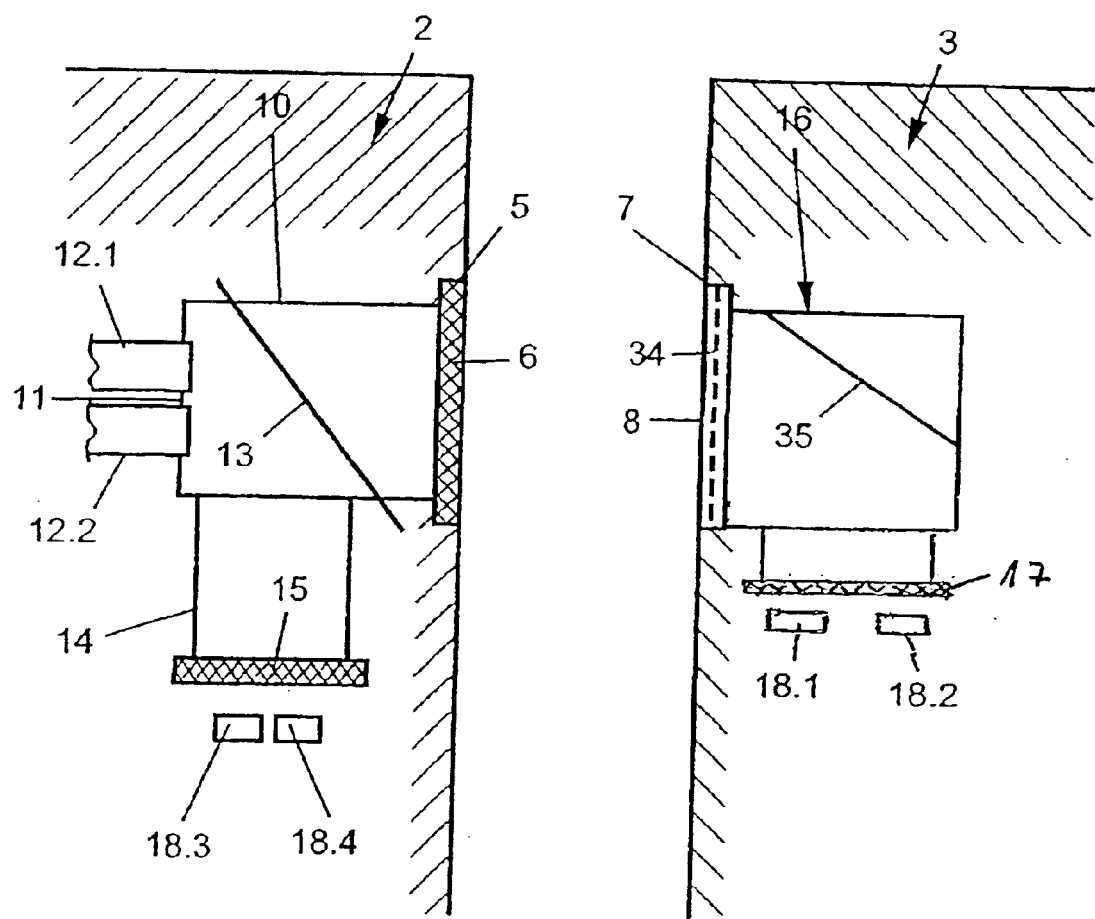
FIG. 3 shows a partial and schematically illustrated detail of a further exemplary embodiment of a device according to the invention similar to figure.

The exemplary embodiment of a device according to the invention according to FIG. 3 differs from that according to FIG. 2 in that a metal grating 34 is provided in the beam path between the transmitters 12.1 and 12.2 and the receivers 18.1 and 18.2, and a deflection mirror 35 is provided in the channel 16. The metal grating 34 is located in the disk 8, but can also be arranged at any other desired point between transmitter around receiver. The metal grating has the advantage that it permits about 80% to 90% of the light to pass through but only about 1% to 0.1% of the electric field. The electric field lines pass through the grating clearances only with difficulty, and most electric field lines are attracted and picked up by the metal grating. By means of this metal grating 34, the sensitivity of the device is increased quite considerably, to be specific to an extent of about 1 to 10 million.

In order to increase this sensitivity once more, the deflection mirror 35 is provided, which deflects the incoming beams for example through 90° onto the receivers 18.1 and 18.2. This increase in the sensitivity of the device is of critical importance in particular in the vicinity, for example, of a submersible pump, from which a great deal of interference originates.

Figure 4:
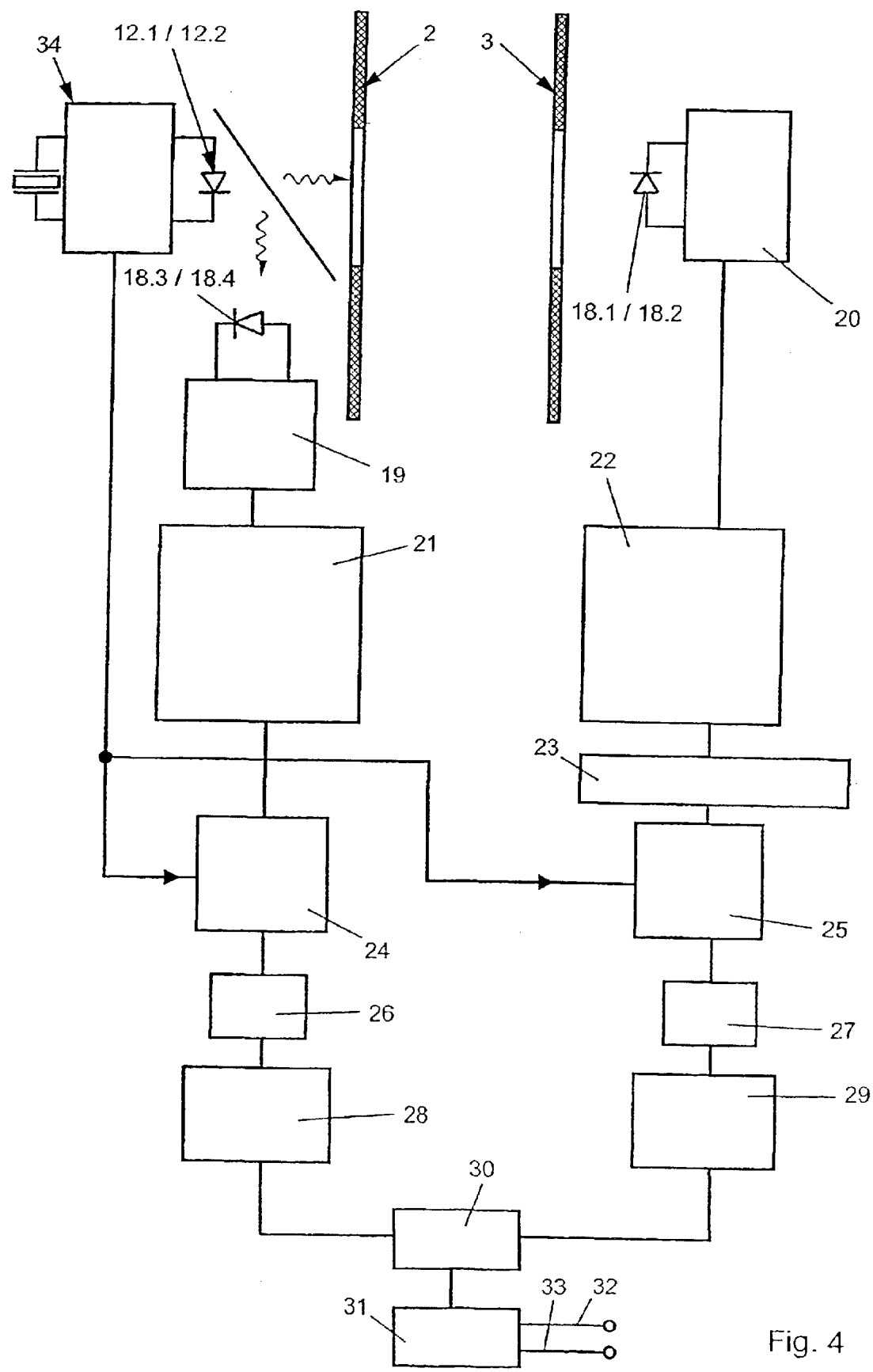
FIG. 4 shows a block-diagram representation of the device and in particular the circuit for the device according to FIG. 1.

According to FIG. 4, the transmitters 12.1 and 12.2 are quartz-stabilized pulse generators for a frequency f. This frequency f is also input in each case into a lock-in amplifier 24 and 25, which are in each case connected into circuits following the receivers 18.3 and 18.4 and 18.1 and 18.2.

Each receiver 18.3/18.4 and 18.1/18.2 is followed by a current-voltage converter 19 and 20, respectively. The signals from this current-voltage converter 19 and 20 then pass into a prefilter 21 and 22 with frequency-selective amplification and constant-light suppression. In this prefilter, those signals whose frequency coincides with the frequency f are particularly emphasized. All other signals are highly attenuated.

An additional amplifier 23 with remotely controllable gain is preferably also arranged downstream of the prefilter 22 in the receiver part.

In both circuits, there next follow the abovementioned lock-in amplifiers 24 and 25, and the low-pass filters 26 and 27 required for their correct function. The functional principle of these subassemblies is sufficiently well known: only those signals whose frequency and phase coincide with the pulse excitation frequency f are passed on. All other signals are highly suppressed. The lock-in amplifiers 24 and 25 in conjunction with the filters 26 and 27 behave like extremely narrow-band and extremely stable band pass filters. At the same time, the phase selectivity leads to high suppression of undesired, capacitively cross-coupled signal components.

The filters 26 and 27 are then in each case followed by an amplifier 28 and 29 with interference signal limitation. Said amplifier has the object of amplifying the measured signal once more and, in addition, of intercepting the known instabilities with very small signals (log(0)=−∞!), known from the usual logarithmic amplifiers, and the negative voltages, which are not permitted.

The measured signal which now results and is unaffected by interference and stray light is fed both from the amplifier 28 and from the amplifier 29 to a logarithmic amplifier 30, which is followed by an output circuit 31 which has two outputs 32 and 33. The solids content, or, in more general terms, the more highly absorbent material component (0–10 volts) can be indicated at the output 32, and the water content or, in more general terms, the more weakly absorbing material component of a mixture composition (0–10 volts) can be indicated at the output 33.

| List of item numbers | |
|---|---|
| 1 | basic housing |
| 2 | housing |
| 3 | housing |
| 4 | interspace |
| 5 | housing opening |
| 6 | filter disk |
| 7 | housing opening |
| 8 | disk |
| 9 | |
| 10 | channel |
| 11 | base |
| 12 | transmitter |
| 13 | mirror disk |
| 14 | channel |
| 15 | filter disk |
| 16 | channel |
| 17 | filter disk |
| 18 | receiver |
| 19 | current-voltage converter |
| 20 | current-voltage converter |
| 21 | prefilter |
| 22 | prefilter |
| 23 | additional amplifier |
| 24 | lock-in amplifier |
| 25 | lock-in amplifier |
| 26 | low-pass filter |
| 27 | low-pass filter |
| 28 | amplifier |
| 29 | amplifier |
| 30 | logarithmic amplifier |
| 31 | output circuit |
| 32 | output |
| 33 | output |
| 34 | metal grating |
| 35 | deflection mirror |
| d | distance |

What is claimed is:

1. A method for determining the mixture composition of any desired media or for measuring the quantity of a material by means of determining the absorption of light, in particular infrared light, which is emitted by a transmitter (12.1, 12.2) into the medium to be examined and whose nonabsorbed and nonreflected constituents are registered by a receiver (18.1, 18.2), the light being sent through the medium directly from transmitter (12.1, 12.2) to receiver (18.1, 18.2), characterized in that the light crosses a channel (10, 16) before and/or after the medium and is scattered at least once, wherein a distance (d) between transmitter (12.1, 12.2) and receiver (18.1, 18.2) is varied.

2. The method as claimed in claim 1, characterized in that part of the light is branched after the transmitter (12.1, 12.2) and is used in a circuit.

3. The method as claimed in claim 2, characterized in that two outputs (32, 33) are provided, so that the mixture composition is indicated.

4. The method as claimed in claim 3, characterized in that the two outputs (32, 33) are balanced by using two material samples which have a different and known mixture composition.

5. The device for determining the mixture composition of any desired media or for measuring the quantity of a material by means of determining the absorption of light, in particular infrared light, which is emitted by a transmitter (12.1, 12.2) into the medium and whose nonabsorbed and nonreflected constituents are registered by a receiver (18.1), 18.2) characterized in that transmitter (12.1, 12.2) and/or receiver (18.1, 18.2) is/are inserted into the interior of a housing (2, 3), remote from a housing opening (5, 7), further including means for varying a distance (d) between transmitter (12.1, 12.2) and receiver (18.1, 18.2).

6. The device as claimed in claim 5, characterized in that at least one scattering filter disk (6, 17) is inserted between transmitter (12.1, 12.2) and receiver (18.1, 18.2).

7. The device as claimed in claim 5, characterized in that transmitter (12.1, 12.2) and/or receiver (18.1, 18.2) are each arranged in a preferably rod-like housing (2, 3).

8. The device as claimed in claim 7, characterized in that two rod-like housings (2, 3) are arranged approximately parallel to one another and leave a distance (4) between them free for the medium to be examined, the housing openings (5, 7) of transmitter (12.1, 12.2) and receiver (18.1, 18.2) being approximately opposite each other.

9. The device as claimed in claim 8, characterized in that a channel (10, 16) is provided between transmitter (12.1, 12.2) and the housing opening (5) assigned to the latter and/or between receiver (18.1, 18.2) and the housing opening (7) assigned to the latter.

10. The device as claimed in claim 9, characterized in that the receiver (18.1, 18.2) provided is a plurality of diodes arranged distributed and having a following current-voltage converter (20).

11. The device as claimed in claim 10, characterized in that the diodes (18.1, 18.2) are arranged at a distance behind a scattering filter disk (17).

12. The device as claimed in claim 11, characterized in that a metal grating is arranged between transmitter (12.1, 12.2) and receiver (18.1, 18.2).

13. The device as claimed in claim 11, characterized in that a deflection mirror is arranged in the channel (16).

14. The device as claimed in claim 13, characterized in that a device (13) for deflecting part of the light is arranged downstream of the transmitter (12.1, 12.2).

15. A device as claimed in claim 14, characterized in that said deflection device is a transparent mirror disk (13).

16. The device as claimed in claim 15, characterized in that the device (13) for deflecting part of the light directs this light onto receivers (18.3, 18.4), in particular diodes, arranged distributed at a distance behind a preferably highly scattering filter disk (15).

17. The device as claimed in claim 16, characterized in that the receivers (18.1, 18.2) are connected to an output circuit (31) via a circuit which includes stray-light suppression.

18. The device as claimed in claim 17, characterized in that the current-voltage converter (19) that determines the quantity of light branched off is likewise connected to an output circuit (31) via a circuit which includes stray light suppression.

19. The device as claimed in claim 18, characterized in that the circuit has a prefilter (21, 22) with frequency-selective amplification and constant-light suppression, an additional amplifier with remotely controllable gain (23), a lock-in amplifier (24, 25), a filter (26, 27), an amplifier (28, 29) with interfering signal limitation and a connection to a logarithmic amplifier (30), which is connected upstream of the output circuit (31).

20. The device as claimed in claim 19, characterized in that the lock-in amplifier (24, 25) in each case has a connection to the transmitter (12.1, 12.2).

21. The device as claimed in claim 20, characterized in that the output circuit (31) has two outputs (32, 33), one for the more highly absorbent material component and the other for the more weakly absorbent material component of a mixture composition.

22. The device as claimed in claim 21, characterized in that the circuit/s are accommodated in a housing (1) from which the preferred housing rods (2, 3) project.

23. The device as claimed in claim 22, characterized in that the preferred housing rods (2, 3) consist of steel, preferably stainless steel.

* * * * *